United States Patent
Fukuchi et al.

(10) Patent No.: US 9,101,137 B2
(45) Date of Patent: Aug. 11, 2015

(54) PEST CONTROL COMPOSITION AND METHOD FOR CONTROLLING PEST

(75) Inventors: Atsushi Fukuchi, Sakuragawa (JP); Naomi Tokoro, Sakuragawa (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/122,886

(22) PCT Filed: May 7, 2012

(86) PCT No.: PCT/JP2012/062240
§ 371 (c)(1), (2), (4) Date: Jan. 13, 2014

(87) PCT Pub. No.: WO2012/165126
PCT Pub. Date: Dec. 6, 2012

(65) Prior Publication Data
US 2014/0163018 A1    Jun. 12, 2014

(30) Foreign Application Priority Data
Jun. 1, 2011 (JP) ................................. 2011-123139

(51) Int. Cl.
| | | |
|---|---|---|
| *A61K 31/535* | (2006.01) | |
| *A61K 31/44* | (2006.01) | |
| *A01N 43/40* | (2006.01) | |
| *A01N 47/12* | (2006.01) | |
| *A01N 31/14* | (2006.01) | |
| *A01N 43/08* | (2006.01) | |
| *A01N 43/56* | (2006.01) | |
| *A01N 43/78* | (2006.01) | |
| *A01N 43/88* | (2006.01) | |
| *A01N 47/08* | (2006.01) | |
| *A01N 53/00* | (2006.01) | |
| *A01N 55/00* | (2006.01) | |

(52) U.S. Cl.
CPC ............... *A01N 43/40* (2013.01); *A01N 31/14* (2013.01); *A01N 43/08* (2013.01); *A01N 43/56* (2013.01); *A01N 43/78* (2013.01); *A01N 43/88* (2013.01); *A01N 47/08* (2013.01); *A01N 47/12* (2013.01); *A01N 53/00* (2013.01); *A01N 55/00* (2013.01)

(58) Field of Classification Search
CPC ....... A01N 47/12; A01N 31/14; A01N 43/40; A01N 43/56; A01N 2300/00; A01N 43/08; A01N 43/78; A01N 43/88; A01N 47/08; A01N 53/00; A01N 55/00; A01N 51/00
USPC ................................................ 514/229.2, 357
See application file for complete search history.

(56) References Cited

U.S. PATENT DOCUMENTS

| | | | |
|---|---|---|---|
| 6,812,229 B1 | 11/2004 | Ozaki et al. | |
| 2008/0214397 A1 | 9/2008 | Forster et al. | |
| 2012/0083463 A1* | 4/2012 | Maue et al. | ..................... 514/30 |

FOREIGN PATENT DOCUMENTS

| | | |
|---|---|---|
| EP | 0963834 A1 | 12/1999 |
| JP | 2006-104097 A | 4/2006 |
| JP | 2007-246495 A | 9/2007 |
| WO | WO 2006/069716 A1 | 7/2006 |
| WO | WO 2010/075994 A1 | 7/2010 |
| WO | WO 2011/039104 A2 | 4/2011 |
| WO | WO 2012/002293 A1 | 1/2012 |

OTHER PUBLICATIONS

Chinese Office Action, issued on Aug. 4, 2014, for Chinese Application No. 201280026225.3.
International Search Report issued in PCT/JP2012/062240 mailed Aug. 7, 2012.
C D S Tomlin, "The Pesticide Manual," Fifteen Edition, Published by BCPC, ISBN 978-1-901396-18-8, 2009, pp. 168-169, 454-455, 1028-1029, 878-879, 442-443, 228-229, 390-391,1112-1113, 816-817 (total 11 sheets).
Shibuya et al., "Shibuya Index (Index of Pesticides)," 13th Edition, Published by Shibuya Index Research Group, Oct. 10, 2008, ISBN 978-4-88137-143-5, 9 pages.
Japanese Office Action and English summary thereof, dated Dec. 10, 2014, for Japanese Application No. 2011-123139.
Chinese Office Action and English translation thereof dated Feb. 28, 2015 for Application No. 201280026225.3.
Kataoka et al., "Mechanism of action and selectivity of a novel fungicide, pyribencarb," Journal of Pesticide Science, vol. 35, No. 2, 2010, pp. 99-106.
The Office Action (including a partial English translation), dated Apr. 30, 2015, issued in the corresponding Chilean Patent Application No. 2013-003420.

* cited by examiner

*Primary Examiner* — My-Chau T Tran
(74) *Attorney, Agent, or Firm* — Birch, Stewart, Kolasch & Birch, LLP

(57) ABSTRACT

[Problem to be Solved] To provide a pest control composition having an excellent controlling activity on pests. [Solution] A pest control composition comprising pyribencarb and at least one insecticide compound selected from Group (A) has an excellent controlling activity on pests: Group (A): the group consisting of cartap hydrochloride, etofenprox, silafluofen, permethrin, ethiprole, clothianidin, dinotefuran, thiamethoxam and nitenpyram.

4 Claims, No Drawings ically, the present invention is the following [1]

PEST CONTROL COMPOSITION AND METHOD FOR CONTROLLING PEST

TECHNICAL FIELD

The present invention relates to a pest control composition and a method for controlling a pest.

BACKGROUND ART

Heretofore, many compounds have been known as active ingredients of pest control compositions (for example, see Non Patent Literatures 1 and 2).

CITATION LIST

Non Patent Literature

[Non Patent Literature 1]
The Pesticide Manual—15th edition (published by BCPC); ISBN 978-1-901396-18-8
[Non Patent Literature 2]
SHIBUYA INDEX (INDEX OF PESTICIDES)—13th edition (published by SHIBUYA INDEX RESEARCH GROUP); ISBN 978-4-88137-143-5

SUMMARY OF INVENTION

Technical Problem

An object of the present invention is to provide a pest control composition having an excellent controlling activity on pests.

Solution to Problem

The present inventors have conducted studies to find a pest control composition having an excellent pest controlling activity on pests, found that the composition containing pyribencarb and a specific insecticide compound exhibits a synergistic effect and has an excellent controlling activity on pests, and accomplished the present invention.

More specifically, the present invention is the following [1] to [4].
[1] A pest control composition comprising pyribencarb and at least one insecticide compound selected from Group (A):
Group (A): the group consisting of cartap hydrochloride, etofenprox, silafluofen, permethrin, ethiprole, clothianidin, dinotefuran, thiamethoxam and nitenpyram.
[2] The pest control composition according to [1], wherein a weight ratio of pyribencarb to the at least one insecticide compound ranges 1000:1 to 1:1000.
[3] A method for controlling a pest comprising the step of applying an effective amount of pyribencarb and at least one insecticide compound selected from Group (A) to a plant or a farm where the plant is cultivated:
Group (A): the group consisting of cartap hydrochloride, etofenprox, silafluofen, permethrin, ethiprole, clothianidin, dinotefuran, thiamethoxam and nitenpyram.
[4] The method according to [3], wherein a weight ratio of pyribencarb to the at least one insecticide compound ranges 1000:1 to 1:1000.

Advantageous Effects of Invention

According to the present invention, pests can be controlled.

DESCRIPTION OF EMBODIMENTS

The pest control composition of the present invention is a composition containing pyribencarb and at least one insecticide compound (hereinafter referred to as the presently recited insecticide compound) selected from Group (A).
Group (A): the group consisting of cartap hydrochloride, etofenprox, silafluofen, permethrin, ethiprole, clothianidin, dinotefuran, thiamethoxam and nitenpyram.

Pyribencarb used in the present invention is a known compound and can be produced by the method described in, for example, WO2001/010825.

Cartap hydrochloride, etofenprox, silafluofen, permethrin, ethiprole, clothianidin, dinotefuran, thiamethoxam and nitenpyram used in the present invention are also all known compounds and described in, for example, The Pesticide Manual-15th edition (published by BCPC); ISBN 978-1-901396-18-8, pages 168, 454, 1029, 879, 443, 229, 391, 1112 and 817. These compounds can be obtained from commercial formulations, or produced by a known method.

In the pest control composition of the present invention, the content ratio of pyribencarb to the presently recited insecticide compounds is not limited, but is usually 0.1 to 1,000 parts by weight, preferably 50 to 1,000 parts by weight, of the total amount of the presently recited insecticide compounds, relative to 100 parts by weight of pyribencarb.

The pest control composition of the present invention may simply be a mixture of pyribencarb and the presently recited insecticide compounds, but is usually used in the form of formulations such as oil solutions, emulsifiable concentrates, flowable formulations, wettable powders, wettable granules, dusts, granules, by mixing pyribencarb, the presently recited insecticide compounds and an inert carrier and adding, as occasion demands, a surfactant and other formulation adjuvants.

Also, the above-formulated pest control compositions can be used as pest control agents per se or after adding other inactive ingredients.

In the pest control composition of the present invention, the total amount of pyribencarb and the presently recited insecticide compounds ranges usually from 0.01 to 99% by weight, preferably from 0.1 to 90% by weight, more preferably from 0.5 to 70% by weight.

Examples of the solid carriers used for formulation include micropowders or granules composed of minerals such as kaolin clay, attapulgite clay, bentonite clay, montmorillonite clay, acid clay, pyrophyllite, talc, diatomaceous earth and calcite; natural organic materials such as corn cob powder and walnut shell flour; synthetic organic material such as urea; salts such as calcium carbonate and ammonium sulfate; and synthetic inorganic materials such as synthetic hydrous silicon oxide. Examples of the liquid carriers include aromatic hydrocarbons such as xylene, alkylbenzene and methylnaphthalene; alcohols such as 2-propanol, ethylene glycol, propylene glycol and ethylene glycol monoethyl ether; ketones such as acetone, cyclohexanone and isophorone; vegetable oils such as soy bean oil and cotton seed oil; aliphatic hydrocarbons from petroleum; esters; dimethylsulfoxide; acetonitrile; and water.

Examples of the surfactants include anionic surfactants such as alkyl sulfonate ester salts, alkylaryl sulfonates, dialkyl sulfosuccinates, polyoxyethylene alkylaryl ether phosphate ester salts, lignosulfonates and naphthalene sulfonate formaldehyde polycondensates; nonionic surfactants such as polyoxyethylene alkylaryl ethers, polyoxyethylene alkyl polyoxypropylene block copolymers and sorbitan fatty acid esters; and cationic surfactants such as alkyltrimethylammonium salts.

Examples of other formulation adjuvants include water-soluble polymers such as polyvinyl alcohol and polyvinyl pyrrolidone; polysaccharides such as gum arabic, alginic acid and salts thereof, CMC (carboxymethylcellulose) and xanthan gum; inorganic substances such as aluminium magnesium silicate and alumina sol; preservatives; coloring agents; and stabilizers such as PAP (acidic isopropyl phosphorate) and BHT.

The pest control composition of the present invention can be used to protect plants from damage of sap-sucking, chewing, etc., caused by harmful insects (e.g., noxious insects and harmful mites).

Examples of the pests on which the pest control composition of the present invention has a controlling activity include the following.

Lepidopteran pests: oriental leafworm moth (*Spodoptera litura*), diamondback moth (*Plutella xylostella*), cabbage white (*Pieris rapaecrucivora*), rice stem borer (*Chilo suppressalis*), beet worm (*Autographa nigrisigna*), oriental tobacco budworm (*Helicoverpa assulta*), armyworm (*Pseudaletia separata*), cabbage moth (*Mamestra brassicae*), summer fruit tortrix (*Adoxophyes oranafasciata*), cotton leafroller (*Notarcha derogata*), rice leaffolder (*Cnaphalocrocis medinalis*), potato tuber moth (*Phthorimaea operculella*), dark-headed rice stem borer (*Chilo polyckysus*), yellow rice borer (*Typoryza incertulas*), small mottled willow moth (*Spodoptera exigua*), turnip moth (*Agrotis segetum*), black cutworm (*Agrotis ipsilon*), corn earworm (*Heliothis armigera*), tobacco budworm (*Heliothis virescens*), cotton bollworm (*Heliothis zea*), rice green semi looper (*Naranga aenescens*), European corn borer (*Ostrinia nubilalis*), Asian corn borer (*Ostrinia furnacalis*), common straight swift (*Parnara guttata*), smaller tea tortrix (*Adoxophyes sp.*), leaf roller (*Caloptilia theivora*), apple leafminer (*Phyllonorycter ringoneella*), peach fruit moth (*Carposina niponensis*), oriental fruit moth (*Grapholita molesta*), codling moth (*Cydia pomonella*), etc.

Hemipteran pests: planthopperses such as small brown planthopper (*Laodelphax striatellus*), brown planthopper (*Nilaparvata lugens*), rice planthoppers (*Sogatella furcifera*); leafhoppers such as green rice leafhopper (*Nephotettix cincticeps*), Taiwanese green rice leafhopper (*Nephotettix virescens*), zigzag leafhopper (*Recilia dorsalis*), tea green leafhopper (*Empoasca onukii*); aphids such as cotton aphid (*Aphis gossypii*), green peach aphid (*Myzus persicae*), Japanese radish aphid (*Brevicoryne brassicae*), spirea aphid (*Aphis spiraecola*), potato aphid (*Macrosiphum euphorbiae*), glasshouse potato aphid (*Aulacorthum solani*), birdcherry-oat aphids (*Rhopalosiphum padi*), black citrus aphid (*Toxoptera citricidus*), mealy plum aphid (*Hyalopterus pruni*), woolly apple aphid (*Eriosoma lanigerum*); stink bugs such as green stink bug (*Nezara antennata*), rice leaf bug (*Trigonotylus caelestialium*), striped bug (*Graphosoma rubrolineatum*), lewis spined bug (*Eysarcoris lewisi*), bean bug (*Riptortus clavetus*), rice bug (*Leptocorisa chinensis*), white spotted spined bug (*Eysarcoris parvus*), brown marmorated stink bug, (*Halyomorpha mista*), southern green stink bug (*Nezara viridula*), tarnished plant bug (*Lygus lineolaris*); whiteflies such as greenhouse whitefly (*Trialeurodes vaporariorum*), sweet potato whitefly (*Bemisia tabaci*), citrus whitefly (*Dialeurodes citri*), orange spiny whitefly (*Aleurocanthus spiniferus*); scale insects such as California red scale (*Aonidiella aurantii*), san Jose scale (*Comstockaspis perniciosa*), citrus snow scale (*Unaspis citri*), red wax scale (*Ceroplastes rubens*), cottony cushion scale (*Icerya purchasi*), Japanese mealybug (*Planococcus kraunhiae*), Cosmstock mealybug (*Pseudococcus longispinis*), white peach scale (*Pseudaulacaspis pentagona*); lace bugs; bed bugs such as common bed bug (*Cimex lectularius*); psyllids such as pear psylla (*Cacopsylla pyricola*).

Thysanoptera pests: thrips such as western flower thrip (*Frankliniella occidentalis*), melon thrip (*Thrips parmi*), yellow tea thrip (*Scirtothrips dorsalis*), onion thrip (*Thrips tabaci*), trybom (*Frankliniella intonsa*), tobacco thrip (*Frankliniella fusca*), onion thrip (*Thrips tabaci*), rice thrip (*Stenchaetothrips biformis*), grass thrip (*Haplothrips aculeatus*).

Among the above pests, suitable examples include crambid moths, planthoppers, whiteflies, aphids and stink bugs.

The pest control composition of the present invention may be used for the purpose of controlling plant diseases and controllable diseases include, but not limited thereto, for example, leaf withering diseases such as rice blast disease (*Magnaporthe grisea*) and rice blight disease (*Cochliobolus miyabeanus*), brown spot disease (*Rhizoctonia solani*); powdery mildew (*Erysiphe graminis*), speckled leaf blotch disease (*Septoria tritici*), glume blotch disease (*Leptosphaeria nodorum*), eye spot disease (*Pseudocercosporella herpotrichoides*), leaf blotch disease (*Rhynchosporium secalis*) in wheats; melanose disease (*Diaporthe citri*), scab disease (*Elsinoe fawcetti*), green mold disease (*Penicillium digitatum, P. italicum*) in citrus fruits; monilia leaf blight disease (*Monilinia mali*), valsa canker disease (*Valsa ceratosperma*), powdery mildew (*Podosphaera leucotricha*), alternaria leaf spot disease (*Alternaria alternata* apple pathotype), scab disease (*Venturia inaequalis*) in apples; scab disease (*Venturia nashicola, V. Pirina*), black spot disease (*Alternaria alternata* Japanese pear pathotype) in pears; brown rot blossom blight and fruit rot disease (*Monilinia fructicola*), scab disease (*Cladosporium carpophilum*), phomopsis rot disease (*Phomopsis* sp.) in peaches; bird's eye rot disease (*Elsinoe ampelina*), ripe rot disease (*Glomerella cingulata*), powdery mildew disease (*Uncinula necator*), rust disease (*Phakopsora ampelopsidis*), black lot disease (*Guignardia bidwellii*), downy mildew disease (*Plasmopara viticola*) in grapes; black spot disease (*Alternaria* sp.), Cylindrosporium leaf spot disease (*Mycosphaerella cerasella*) in sweet cherry; brown rot blossom blight and fruit rot disease (*Monilinia fructicola*) in Japanese plum; brown rot blossom blight and fruit rot disease (*Monilinia fructicola*) in apricot; scab disease (*Cladosporium carpohilum*) in plums; anthracnose disease (*Gloeosporium kaki*), angular leaf spot disease (*Cercospora kaki, Mycosphaerella nawae*) in Japanese persimmons; anthracnose disease (*Colletotrichum lagenarium*), powdery mildew disease (*Sphaerotheca fuliginea*), gummy stem blight disease (*Mycosphaerella melonis*), fusarium wilt disease (*Fusarium oxysporum*), downy mildew disease (*Pseudoperonospora cubensis*), Phytophthora rot (*Phytophthora* sp.), seedling blight disease (*Pythium* sp.) in cucurbitaceous fruits; early blight disease (*Alternaria solani*), leaf mold disease (*Cladosporium fulvum*), late blight disease (*Phytophthora infestans*) in tomatoes; brown spot disease (*Phomopsis vexans*), powdery mildew disease (*Erysiphe cichoracearum*) in eggplants; alternaria leaf spot disease (*Alternaria japonica*), white spot disease (*Cercosporella brassicae*) in Brassicaceae vegetables; rust disease (*Puccinia allii*) in leeks; purple speck disease (*Cercospora kikuchii*), sphaceloma scab (*Elsinoe glycines*), pod and stem blight disease (*Diaporthe phaseolorum varsojae*), rust disease (*Phakopsora pachyrhizi*) in soybean; anthracnose disease (*Colletotrichum lindemthianum*) in common beans; leaf spot disease (*Cercospora personata*), brown leaf spot disease (*Cercospora*

*arachidicola*) in peanut; mild mildew disease (*Erysiphe pisi*) in peas; early blight disease (*Alternaria solani*), late blight disease (*Phytophthora infestans*) in potatoes; mild mildew (*Sphaerotheca humuli*) in strawberries; early blight disease (*Pestalotiopsis longiseta, Pestalotiopsis theae*), anthracnose disease (*Colletotrichum theae-sinensis*), tea shoot bright disease (*Pestalotiopsis longiseta*), Japanese exobasidium blight disease (*Exobasidium reticulatum*), white scab disease (*Elsinoe leucospila*) in teas; brown spot disease (*Alternaria longipes*), mild mildew disease (*Erysiphe cichoracearum*), anthracnose disease (*Colletotrichum tabacum*), downy mildew disease (*Peronospora tabacina*), late blight disease (*Phytophthora nicotianae*) in tobacco; cercospora leaf spot disease (*Cercospora beticola*) in sugar beet; scab disease (*Diplocarpon rosae*), mild mildew disease (*Sphaerotheca pannosa*) in roses; brown leaf spot disease (*Septoria chrysanthemi-indici*), rust disease (*Puccinia horiana*) in chrysanthemums; gray mold disease (*Botrytis cinerea*), stem rot disease (*Sclerotinia sclerotiorum*) in various farm crops; black spot disease (*Alternaria brassicicola*) in Japanese radish; dollar spot disease (*Sclerotinia homeocarpa*), brown patch disease and large patch disease (*Rhizoctonia solani*) in bentgrass; etc.

The pest control composition of the present invention is used to control pests by applying it to a plant or a farm where the plant is cultivated. The plant herein includes plant stems and leaves, plant flowers, plant fruits and plant seeds.

The method for controlling a pest of the present invention is carried out by applying the pest control composition of the present invention, and specific examples include the application to plant stems and leaves such as foliar spraying, soil application and water surface application.

When the pest composition of the present invention is applied to a plant or a farm where the plant is cultivated, the amount applied can be varied depending on the type of a plant to be treated, the type and frequency of infestation of a pest to be controlled, formulation forms, application timing, climate conditions, etc., however, the total amount of pyribencarb and the presently recited insecticide compounds ranges usually 0.5 to 100,000 g, preferably 5 to 10,000 g, relative to 10,000 $m^2$ of the area in which the target plant is cultivated.

The emulsifiable concentrates, wettable powders and flowable formulations are sprayed usually after being diluted with water. In such a case, the total concentration of pyribencarb and the presently recited insecticide compounds ranges usually from 0.0001 to 10% by weight, preferably from 0.0001 to 5% by weight. The dusts, granules and the like are usually applied per se without dilution.

The method for controlling a pests of the present invention can be used for farmlands such as fields, paddy fields, well-drained paddy fields, lawn and orchards, or for non-farmlands.

Farm crops: corn, rice, wheat, barley, rye wheat, oat, sorghum, cotton, soybeans, peanut, buckwheat, sugar beet, rapeseed, sunflower, sugarcane, tobacco, etc.

Vegetables; solanaceae vegetables (eggplant, tomato, green pepper, capsicum, potato, etc.), cucurbitaceae vegetables (cucumber, Japanese pumpkin, zucchini, watermelon, melon, etc.), brassicaceae vegetables (rape, Japanese radish, turnip, horseradish, kohlrabi, Chinese cabbage, cabbage, mustard, broccoli, cauliflower, etc.), asteraceae vegetables (burdock, garland chrysanthemum, artichoke, lettuce, etc.), liliaceae vegetables (leek, onion, garlic, asparagus, etc.), apiaceae vegetables (carrot, parsley, celery, parsnip etc.), chenopodiaceae vegetables (spinach, Swiss chard, etc.), labiatae vegetables (beafsteak plant, mint, basil, etc.), strawberries, sweet potato, yam, taro, etc.

Fruit trees: kernel fruits (apple, pear, Japanese pear, Chinese quince, quince, etc.), stone fruits (peach, Japanese plum, nectarine, plum, sweet cherry, apricot, prune, etc.), citrus fruits (satsuma mandarin, oranges, lemon, lime, grapefruit, etc.), nut trees (chestnut, walnut, hazel, almond, pistachio, cashew nut, macadamia nut, etc.), berry fruits (blueberry, cranberry, blackberry, raspberry, etc.), grapes, persimmon, olive, loquat, banana, coffee, date, coconut palm, oil palm, etc.

Trees other than fruit trees: tea, mulberry, ornamental trees and shrubs (azalea, camellia, hydrangea, sasanqua, Japanese star anise, cherry tree, tulip tree, crape myrtle, orange sweet tea, etc.), roadside trees (ash tree, birch tree, dogwood, eucalyptus, ginkgo tree, lilac, maple, oak tree, poplar, Chinese redbud, formosan sweetgum, plane tree, zelkova, Japanese Thuja, *Abies firma*, hemlock fir, needle juniper, pine, spruce, yew tree, elm tree, Japanese horse chestnut, etc.), sweet viburnum, yew plum pine, cedar, cypress, croton, Japanese spindletree, Japanese photinia, etc.

Lawn: lawn grasses (zoysiagrass, Korean lawn grass, etc.), Bermuda glasses (*cynodon dactylon*, etc.), bentgrasses (redtop grass, creeping bentgrass, colonial bentgrass, etc.), bluegrasses (Kentucky bluegrass, rough bluegrass, etc.), fescue grasses (tall fescue, chewings fescue, creeping red fescue, etc.), perennial ryegrasses, (Italian ryegrass, perennial flax, etc.), orchard grass, timothee, etc.

Others: flowering plants (roses, carnation, chrysanthemum, Texas bluebell, baby's breath, gerbera, marigold, salvia, petunia, verbena, tulip, aster, gentian, lily, pansy, cyclamen, orchid, lily of the valley, lavender, stock, ornamental cabbage, primula, poinsettia, gladiolus, cattleya, daisy, cymbidium, begonia, etc.), biomass energy plants (jatropha, safflower, camelia alyssum, switchgrass, monkey grass, reed canarygrass, arundo donax, kenaf, cassava, willow, etc.), decorative plants, etc.

Among the above plants, suitable examples are corn, wheat, rice, etc. Rice is suitable among these.

The above "plants" may be those provided with resistance by gene modification technology or a cross breeding technique.

EXAMPLES

The present invention will be described below in further detail with reference to Formulation Examples and Test Examples, but is not limited thereto. In the following examples, the term "parts" indicates "parts by weight" unless otherwise indicated.

Formulation Examples will first be given.

Formulation Example 1

15 Parts of pyribencarb and 15 parts of cartap hydrochloride are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 2

15 Parts of pyribencarb and 15 parts of etofenprox are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 3

15 Parts of pyribencarb and 15 parts of silafluofen are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 4

15 Parts of pyribencarb and 15 parts of dinotefuran were added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 5

15 Parts of pyribencarb and 15 parts of ethiprole are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 6

15 Parts of pyribencarb and 15 parts of thiamethoxam are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 7

15 Parts of pyribencarb and 15 parts of permethrin are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 8

15 Parts of pyribencarb and 15 parts of clothianidin are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 9

15 Parts of pyribencarb and 15 parts of nitenpyram are added to a mixture of 4 parts of sodium lauryl sulfate, 2 parts of calcium lignin sulfonate, 20 parts of synthetic hydrous silicon oxide micropowder and 44 parts of diatomaceous earth, and the resultant mixture is stirred and mixed thoroughly to obtain a wettable powder.

Formulation Example 10

1 Part of pyribencarb, 2 parts of cartap hydrochloride, 87 parts of kaolin clay and 10 parts of talc are pulverized and mixed thoroughly to obtain a dust.

Formulation Example 11

1 Part of pyribencarb, 2 parts of etofenprox, 87 parts of kaolin clay and 10 parts of talc are pulverized and mixed thoroughly to obtain a dust.

Formulation Example 12

1 Part of pyribencarb, 2 parts of silafluofen, 87 parts of kaolin clay and 10 parts of talc are pulverized and mixed thoroughly to obtain a dust.

Formulation Example 13

1 Part of pyribencarb, 2 parts of dinotefuran, 87 parts of kaolin clay and 10 parts of talc are pulverized and mixed thoroughly to obtain a dust.

Formulation Example 14

1 Part of pyribencarb, 2 parts of ethiprole, 87 parts of kaolin clay and 10 parts of talc are pulverized and mixed thoroughly to obtain a dust.

Formulation Example 15

1 Part of pyribencarb, 2 parts of thiamethoxam, 87 parts of kaolin clay and 10 parts of talc are pulverized and mixed thoroughly to obtain a dust.

Formulation Example 16

1 Part of pyribencarb, 2 parts of permethrin, 87 parts of kaolin clay and 10 parts of talc are pulverized and mixed thoroughly to obtain a dust.

Formulation Example 17

1 Part of pyribencarb, 1.5 parts of clothianidin, 87 parts of kaolin clay and 10 parts of talc are pulverized and mixed thoroughly to obtain a dust.

Formulation Example 18

1 Part of pyribencarb, 1.5 parts of nitenpyram, 87 parts of kaolin clay and 10 parts of talc are pulverized and mixed thoroughly to obtain a dust.

Formulation Example 19

10 Parts of pyribencarb, 10 parts of cartap hydrochloride, 30 parts of white carbon containing 50 parts of ammonium salt of polyoxyethylene alkyl ether sulfate and 50 parts of water are mixed and pulverized by a wet milling method to obtain a flowable formulation.

Formulation Example 20

10 Parts of pyribencarb, 10 parts of etofenprox, 30 parts of white carbon containing 50 parts of ammonium salt of polyoxyethylene alkyl ether sulfate and 50 parts of water are mixed and pulverized by a wet milling method to obtain a flowable formulation.

Formulation Example 21

10 Parts of pyribencarb, 10 parts of silafluofen, 30 parts of white carbon containing 50 parts of ammonium salt of polyoxyethylene alkyl ether sulfate and 50 parts of water are mixed and pulverized by a wet milling method to obtain a flowable formulation.

Formulation Example 22

10 Parts of pyribencarb, 10 parts of dinotefuran, 30 parts of white carbon containing 50 parts of ammonium salt of polyoxyethylene alkyl ether sulfate and 50 parts of water are mixed and pulverized by a wet milling method to obtain a flowable formulation.

Formulation Example 23

10 Parts of pyribencarb, 10 parts of ethiprole, 30 parts of white carbon containing 50 parts of ammonium salt of polyoxyethylene alkyl ether sulfate and 50 parts of water are mixed and pulverized by a wet milling method to obtain a flowable formulation.

Formulation Example 24

10 Parts of pyribencarb, 10 parts of thiamethoxam, 30 parts of white carbon containing 50 parts of ammonium salt of polyoxyethylene alkyl ether sulfate and 50 parts of water are mixed and pulverized by a wet milling method to obtain a flowable formulation.

Formulation Example 25

10 Parts of pyribencarb, 10 parts of permethrin, 30 parts of white carbon containing 50 parts of ammonium salt of polyoxyethylene alkyl ether sulfate and 50 parts of water are mixed and pulverized by a wet milling method to obtain a flowable formulation.

Formulation Example 26

10 Parts of pyribencarb, 10 parts of clothianidin, 30 parts of white carbon containing 50 parts of ammonium salt of polyoxyethylene alkyl ether sulfate and 50 parts of water are mixed and pulverized by a wet milling method to obtain a flowable formulation.

Formulation Example 27

10 Parts of pyribencarb, 10 parts of nitenpyram, 30 parts of white carbon containing 50 parts of ammonium salt of polyoxyethylene alkyl ether sulfate and 50 parts of water are mixed and pulverized by a wet milling method to obtain a flowable formulation.

Next, the effects of the present invention will be demonstrated with reference to Test Examples.

Test Example 1

10 mg of each of pyribencarb, cartap hydrochloride, dinotefuran, clothianidin, nitenpyram and thiamethoxam was each dissolved in 1 ml of acetone (manufactured by Wako Pure Chem Industries, Ltd.) containing Sorgen TW-20 (manufactured by Dai-ichi Kogyo Seiyaku Co., Ltd) and each solution was diluted with water containing 0.02% by volume of a spreader (trade name: Dain (registered trade name), manufactured by Sumitomo Chemical Takeda Agro Company) to attain a predetermined concentration. The water-diluted solution of pyribencarb was mixed with the water-diluted solution of cartap hydrochloride, dinotefuran, clothianidin, nitenpyram or thiamethoxam to prepare test sample solutions.

Seeds were sown into plastic pots containing potting soil and raised for about 15 days. To rice (*Oryza sativa*, variety: Nanatsuboshi) having the third true leaves completely unfolded, 10 ml of each of the test sample solutions per pot was applied by spraying using a spray gun. After air drying, the pots, together with the rice plants which developed rice blast disease, were allowed to stand for 24 hours at 25° C. in a moist room (humidity 95 to 100%). Subsequently, the rice plants developed rice blast disease were separated and grown for 6 days in the moist room described above and measured for the lesion area percentage (the lesion area percentage of a treated area). The tests were carried out in duplicate.

Rice plants were grown in the same manner as above except that the test sample solutions were not sprayed and measured for the lesion area percentage (the lesion area percentage of an untreated area). The control values were calculated by the following equation 1).

control value=100×(*A*−*B*)/*A*  Equation 1);

A: lesion area percentage of untreated area
B: lesion area percentage of treated area
The average values thereof are shown in Table 1.

TABLE 1

| Test compound | Application concentration (ppm) | Control value |
| --- | --- | --- |
| Pyribencarb | 10 | 18.8 |
| Pyribencarb + Cartap hydrochloride | 10 + 100 | 68.8 |
| Pyribencarb + Dinotefuran | 10 + 100 | 50.0 |
| Pyribencarb + Clothianidin | 10 + 100 | 37.5 |
| Pyribencarb + Nitenpyram | 10 + 100 | 43.8 |
| Pyribencarb + Thiamethoxam | 10 + 100 | 31.3 |

Test Example 2

10 mg of each of pyribencarb, permethrin, ethiprole and nitenpyram was each dissolved in 1 ml of acetone (manufactured by Wako Pure Chem Industries, Ltd.) containing Sorgen TW-20 (manufactured by Dai-ichi Kogyo Seiyaku Co., Ltd) and each solution was diluted with water containing 0.02% by volume of a spreader (trade name: Dain (registered trade name), manufactured by Sumitomo Chemical Takeda Agro Company) to attain a predetermined concentration. The water-diluted solution of pyribencarb was mixed with the water-diluted solution of permethrin, ethiprole or nitenpyram to prepare test sample solutions.

Seeds were sown into plastic pots containing potting soil and raised for about 15 days. To rice (*Oryza sativa*, variety: Nanatsuboshi) having the third true leaves completely unfolded, 10 ml of each of the test sample solutions per pot was applied by spraying using a spray gun. After air drying, the pots, together with the rice plants which developed rice blast disease, were allowed to stand for 24 hours at 25° C. in a moist room (humidity 95 to 100%). Subsequently, the rice plants developed rice blast were separated and grown for 5 days in the moist room described above and measured for the lesion area percentage (the lesion area percentage of a treated area). The tests were carried out in duplicate.

Rice plants were grown in the same manner as above except that the test sample solutions were not sprayed and measured for the lesion area percentage (the lesion area percentage of an untreated area). The control values were calculated by the following equation 1).

$$\text{control value} = 100 \times (A-B)/A \quad \text{Equation 1)};$$

A: lesion area percentage of untreated area

B: lesion area percentage of treated area

Table 2 shows the results.

TABLE 2

| Test compound | Application concentration (ppm) | Control value |
|---|---|---|
| Pyribencarb | 20 | 40.0 |
| Pyribencarb + Permethrin | 20 + 10 | 60.0 |
| Pyribencarb + Ethiprole | 20 + 100 | 86.0 |
| Pyribencarb + Nitenpyram | 20 + 100 | 60.0 |

Test Example 3

10 mg of each of pyribencarb, cartap hydrochloride, etofenprox, silafluofen, dinotefuran, ethiprole, thiamethoxam, permethrin, clothianidin and nitenpyram was each dissolved in 1 ml of acetone (manufactured by Wako Pure Chem Industries, Ltd.) containing Sorgen TW-20 (manufactured by Dai-ichi Kogyo Seiyaku Co., Ltd) and each solution was diluted with water containing 0.02% by volume of a spreader (trade name: Dain (registered trade name), manufactured by Sumitomo Chemical Takeda Agro Company) to attain a predetermined concentration. The water-diluted solution of pyribencarb was mixed with the water-diluted solution of cartap hydrochloride, etofenprox, silafluofen, dinotefuran, ethiprole, thiamethoxam, permethrin, clothianidin or nitenpyram to prepare test sample solutions.

Seeds were sown into plastic pots containing potting soil and raised for about 15 days. To rice (Oryza sativa, variety: Nanatsuboshi) having the third true leaves completely unfolded, 10 ml of each of the test sample solutions per pot was applied by spraying using a spray gun. After air drying, the pots, together with the rice plants which developed rice blast disease, were allowed to stand for 24 hours at 25° C. in a moist room (humidity 95 to 100%). Subsequently, the rice plants developed rice blast disease were separated and grown for 6 days in the moist room described above and measured for the lesion area percentage (the lesion area percentage of a treated area). The tests were carried out in duplicate.

Rice plants were grown in the same manner as above except that the test sample solutions were not sprayed and measured for the lesion area percentage (the lesion area percentage of an untreated area). The control values were calculated by the following equation 1).

$$\text{control value} = 100 \times (A-B)/A \quad \text{Equation 1)};$$

A: lesion area percentage of untreated area

B: lesion area percentage of treated area

Table 3 shows the results.

TABLE 3

| Test compound | Application concentration (ppm) | Control value |
|---|---|---|
| Pyribencarb | 50 | 86.0 |
| Pyribencarb + Cartap hydrochloride | 50 + 50 | 94.0 |
| Pyribencarb + Etofenprox | 50 + 50 | 99.0 |
| Pyribencarb + Silafluofen | 50 + 50 | 99.0 |
| Pyribencarb + Dinotefuran | 50 + 50 | 92.0 |
| Pyribencarb + Ethiprole | 50 + 50 | 100 |
| Pyribencarb + Thiamethoxam | 50 + 50 | 92.0 |
| Pyribencarb + Permethrin | 50 + 50 | 96.0 |
| Pyribencarb + Clothianidin | 50 + 50 | 92.0 |
| Pyribencarb + Nitenpyram | 50 + 50 | 92.0 |

Test Example 4

10 mg of each of pyribencarb and cartap hydrochloride was each dissolved in 1 ml of acetone (manufactured by Wako Pure Chem Industries, Ltd.) containing Sorgen TW-20 (manufactured by Dai-ichi Kogyo Seiyaku Co., Ltd) and each solution was diluted with water containing 0.02% by volume of a spreader (trade name: Dain (registered trade name), manufactured by Sumitomo Chemical Takeda Agro Company) to attain a predetermined concentration. The water-diluted solution of pyribencarb was mixed with the water-diluted solution of cartap hydrochloride to prepare test sample solutions.

10 mL of each of the test sample solutions per plant was sprayed to 2.5 leaf stage seedlings of rice (Oryza sativa, variety: Nanatsuboshi) planted in a paper pot. After air drying, the rice seedlings were placed in plastic cups (diameter 90 mm, height 30 mm) containing water. Ten first instar larvae of rice leaffolder were released in the cups and the cups were placed in a room (25° C., humidity 60%). Three days later, the larvae subjected to the test were observed for dead or alive. Based on the observation results, the insect mortality was calculated by equation 2) and the adjusted insect mortality was calculated by equation 3). The tests were carried out in duplicate. The average values thereof are shown in Table 4.

$$\text{insect mortality (\%)} = \text{number of dead insects in treated area/number of insect tested} \times 100 \quad \text{Equation 2)};$$

$$\text{adjusted insect mortality (\%)} = \{(\text{insect mortality in treated area} - \text{insect mortality in untreated area})/(100 - \text{insect mortality in untreated area})\} \times 100 \quad \text{Equation 3)};$$

TABLE 4

| Test compound | Application concentration (ppm) | Adjusted insect mortality (%) |
|---|---|---|
| Pyribencarb | 10 | 0.0 |
| Cartap hydrochloride | 100 | 52.6 |
| Pyribencarb + Cartap hydrochloride | 10 + 100 | 100 |

Test Example 5

10 mg of each of pyribencarb, etofenprox, silafluofen and ethiprole was each dissolved in 1 ml of acetone (manufactured by Wako Pure Chem Industries, Ltd.) containing Sorgen TW-20 (manufactured by Dai-ichi Kogyo Seiyaku Co., Ltd) and each solution was diluted with water containing 0.02% by volume of a spreader (trade name: Dain (registered trade name), manufactured by Sumitomo Chemical Takeda Agro Company) to attain a predetermined concentration. The water-diluted solution of pyribencarb was mixed with the water-diluted solution of etofenprox, silafluofen or ethiprole to prepare test sample solutions.

10 mL of each of the test sample solutions per pot was sprayed to 2.5 leaf stage seedlings of rice (*Oryza sativa*, variety: Nanatsuboshi) planted in a paper pot. After air drying, the rice seedlings were placed in plastic cups (diameter 90 mm, height 30 mm) containing water. Ten first instar larvae of rice leaffolder were released in the cups and the cups were placed in a room (25° C., humidity 60%). Four days later, the larvae subjected to the test were observed for dead or alive. Based on the observation results, the insect mortality was calculated by equation 2) and the adjusted insect mortality was calculated by equation 3), as described in Test Example 4. The tests were carried out in duplicate. The average values thereof are shown in Table 5.

TABLE 5

| Test compound | Application concentration (ppm) | Adjusted insect mortality (%) |
| --- | --- | --- |
| Pyribencarb | 20 | 0.0 |
| Etofenprox | 10 | 52.9 |
| Silafluofen | 10 | 23.5 |
| Ethiprole | 100 | 35.3 |
| Pyribencarb + Etofenprox | 20 + 10 | 64.7 |
| Pyribencarb + Silafluofen | 20 + 10 | 47.1 |
| Pyribencarb + Ethiprole | 20 + 100 | 70.6 |

Test Example 6

10 mg of each of pyribencarb and dinotefuran was each dissolved in 1 ml of acetone (manufactured by Wako Pure Chem Industries, Ltd.) containing Sorgen TW-20 (manufactured by Dai-ichi Kogyo Seiyaku Co., Ltd) and each solution was diluted with water containing 0.02% by volume of a spreader (trade name: Dain (registered trade name), manufactured by Sumitomo Chemical Takeda Agro Company) to attain a predetermined concentration. The water-diluted solution of pyribencarb was mixed with the water-diluted solution of dinotefuran to prepare test sample solutions.

10 mL of each of the test sample solutions per pot was sprayed to 2.5 leaf stage seedlings of rice (*Oryza sativa*, variety: Nanatsuboshi) planted in a paper pot. After air drying, the rice seedlings were placed in plastic cups (diameter 90 mm, height 30 mm) containing water. Ten first instar larvae of rice leaffolder were released in the cups and the cups were placed in a room (25° C., humidity 60%). Four days later, the larvae subjected to the test were observed for dead or alive. Based on the observation results, the insect mortality was calculated by equation 2) and the adjusted insect mortality was calculated by equation 3), as described in Test Example 4. The tests were carried out in duplicate. The average values thereof are shown in Table 6.

TABLE 6

| Test compound | Application concentration (ppm) | Adjusted insect mortality (%) |
| --- | --- | --- |
| Pyribencarb | 100 | 0.0 |
| Dinotefuran | 100 | 57.9 |
| Pyribencarb + Dinotefuran | 100 + 100 | 89.5 |

The invention claimed is:

1. A pest control composition comprising pyribencarb and at least one insecticide compound selected from Group (A):
   Group (A): the group consisting of cartap hydrochloride, etofenprox, silafluofen, permethrin, ethiprole, clothianidin, dinotefuran, thiamethoxam and nitenpyram.

2. The pest control composition according to claim 1, wherein a weight ratio of pyribencarb to the at least one insecticide compound ranges 1000:1 to 1:1000.

3. A method for controlling a pest comprising the step of applying an effective amount of pyribencarb and at least one insecticide compound selected from Group (A) to a plant or a farm where the plant is cultivated:
   Group (A): the group consisting of cartap hydrochloride, etofenprox, silafluofen, permethrin, ethiprole, clothianidin, dinotefuran, thiamethoxam and nitenpyram.

4. The method according to claim 3, wherein a weight ratio of pyribencarb to the at least one insecticide compound ranges 1000:1 to 1:1000.

* * * * *